United States Patent [19]

Carter et al.

[11] Patent Number: 5,188,945
[45] Date of Patent: Feb. 23, 1993

[54] RECOVERY PROCESS FOR ANTIBIOTICS LL-E19020 ALPHA AND BETA

[75] Inventors: Guy T. Carter, Suffern; David R. Williams, Stony Point; Fernando Pinho, Valley Cottage, all of N.Y.

[73] Assignee: American Cyanamid Company, Stamford, Conn.

[21] Appl. No.: 756,634

[22] Filed: Sep. 9, 1991

[51] Int. Cl.$^5$ .................. C12P 19/58; C12P 1/04
[52] U.S. Cl. ...................... 435/77; 435/170; 435/803; 536/16.8; 536/16.9
[58] Field of Search .............. 435/170, 803, 77; 536/16.9, 16.8

[56] References Cited

U.S. PATENT DOCUMENTS

| | | | |
|---|---|---|---|
| 4,091,201 | 5/1978 | Argoudelis | 536/16.9 |
| 4,252,971 | 2/1981 | Harrison | 536/16.9 |
| 4,380,625 | 4/1983 | Stadler et al. | 536/16.9 |
| 4,568,740 | 2/1986 | Oppici et al. | 536/16.9 |
| 4,704,276 | 11/1987 | Kantor | 435/169 |
| 4,705,688 | 11/1987 | Carter et al. | 435/169 |
| 4,861,870 | 8/1989 | Oppici et al. | 536/16.9 |
| 5,077,277 | 12/1991 | Phillipson et al. | 536/168 |

OTHER PUBLICATIONS

Amberlite Ion Exchange Resins, Catalog No. R-31-3.
Amberlite XAD-2, Technical Bulletin Ion Exchange Dept. pp. 1-8.
Amberlite XAD-4, Preliminary Technical Notes, pp. 1-10.
Amberlite XAD-7, Preliminary Technical Notes, pp. 1-10.
Amberlite XAD-16, Polymeric Adsorbent Product Data Sheet, pp. 1 and 2.

*Primary Examiner*—Herbert J. Lilling
*Attorney, Agent, or Firm*—T. S. Szatkowski

[57] ABSTRACT

The invention provides an improved process for the isolation and purification of antibiotics designated LL-E19020 alpha and beta which are derived from the microorganism *Streptomyces lydicus* ssp. tanzanius NRRL 18036.

The invention is a method of recovery, concentration from crude solutions and to processes for the purification of anitbiotics designated LL-E19020 alpha and beta which are derived from the microorganism *Streptomyces lydicus* ssp. tanzanius NRRL 18036.

12 Claims, No Drawings

RECOVERY PROCESS FOR ANTIBIOTICS LL-E19020 ALPHA AND BETA

BACKGROUND OF THE INVENTION

1. Field of the Invention

The invention relates to a new process for the recovery and purification of the antibiotics LL-E19020 alpha and LL-E19020 beta from crude solutions and to processes for their purification.

2. Description of the Prior Art

Antibiotics LL-E19020 alpha and LL-E19020 beta are disclosed in U.S. Pat. No. 4,705,688, The Journal Of Antibiotics, 41(10), 1511–1514 (1988) and The Journal Of Antibiotics, 42(10), 1489–1493 (1989). Antibiotic LL-E19020 alpha has a phenylacetate ester group attached at C-23 and has the structure:

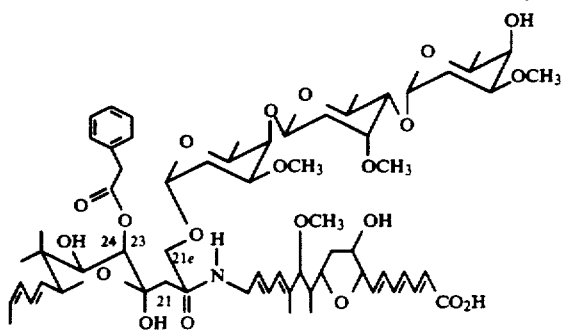

Antibiotic LL-E19020 beta ha a phenylacetate ester group attached at C-24 and has the structure:

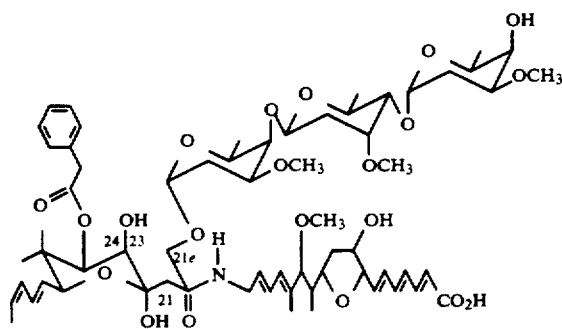

A process for purification of the antibiotic LL-E19020 alpha by reversed phase HPLC purification is described in Journal Of Chromatography, 484, 381–390- (1989). Antibiotics LL-E19020 alpha and LL-E19020 beta are also useful for increasing the growth rate of meat producing animals and for treating respiratory disease, fowl cholera and necrotic enteritis as described in U.S. Pat. Nos. 4,704,276 and 4,968,493.

A related family of compounds, the phenelfamycins, is reported in The Journal Of Antibiotics, 41(10), 1293–1299 (1988); The Journal Of Antibiotics, 41(10), 1300–1315 (1988): The Journal Of Antibiotics, 39(10), 1361–1367 (1986); The Journal Of Antibiotics, 42(1), 94–101 (1989); Antimicrobiol Agents and Chemotherapy, 33(3), 322–325 (1989); Program and Abstracts Of The 27th Interscience Conference on Antimicrobial Agents Chemotherapy, No. 995, p 270, New York, Oct. 4–7, 1987.

Although the process for the isolation and purification of LL-E19020 alpha and LL-E19020 beta as described in the aforementioned references works well for small scale fermentations the new process, as described in this application, works much better for large scale fermentations by having fewer manipulative steps and affords product with higher purity.

SUMMARY OF THE INVENTION

This invention provides an improvement in the large-scale recovery of LL-E19020 alpha and LL-E19020 beta. The improvement comprises: (1) adsorbing the antibiotic from the fermentation medium in which it is produced onto a nonionic adsorption resin(high porous copolymer), typical examples thereof include styrene-divinylbenzene type copolymers, substituted styrene-divinylbenzene type copolymers; methacrylic acid type polymers, styrene-allylacrylate type copolymers, other vinyl polymers or copolymers, and the like polymers which have been formed into granules; (2) separating the resin from the fermentation broth in the batch mode or filtering an aqueous organic solvent solution of the broth through a resin column; (3) eluting the antibiotic from the resin and (4) purifying the fractions by methods such as chromatography, precipitation, crystallization or freeze-drying. The advantages of this improved process are (1) the number of manipulative steps is decreased and (2) the material obtained is of higher purity.

The isolation of pure kilogram quantities of LL-E19020 alpha and LL-E19020 beta from fermentation medium is not an easy task. The fermentation medium is a complex mixture of many unwanted materials. Conditions which work well to isolate products needed for research purposes may not be acceptable for larger quantities.

A new process has been found for the recovery and purification of antibiotics LL-E19020 alpha and LL-E19020 beta from fermentation medium using a nonionic adsorption resin(high porous copolymer). The use of this resin is novel to these antibiotics. The resin optimizes the quantity of antibiotics recoverable from the fermentation medium and allows for the removal of trace impurities through washing of the column with water without removal of the products. In addition, the elution of the column with step gradients of acetone-water allows for the partial purification of the antibiotics on a large scale. The collected fractions can be further purified by high pressure liquid chromatography (HPLC).

DESCRIPTION OF THE PREFERRED EMBODIMENTS

The antibiotics LL-E19020 alpha and beta are produced by fermentation of a strain of *Streptomyces lydicus*, ssp. *tanzanius*, NRRL 18036, in an aqueous nutrient medium containing assimilable sources of carbon and nitrogen under submerged aerobic conditions. This microorganism is maintained in the culture collection of the Medical Research Division, American Cyanamid Company, Pearl River, N.Y. as culture number LL-E19020. A viable culture of this new microorganism has been deposited with the Patent Culture Collection Laboratory, Northern Regional Research Center, U.S. Department of Agriculture, Peoria, Ill. 61604, and has been added to its permanent collection. It has been assigned the strain designation NRRL 18036 by said depository.

It is to be understood that for the production of these antibacterial agents the present invention is not limited to this particular organism or to organisms fully answering the above characteristics which are given for illustrative purposes only. In fact, it is desired and intended to include the use of mutants produced from this organism by various mean such as exposure of X-radiation, ultraviolet radiation, N'-methyl-N'-nitro-N-nitrosoguanidine, actinophages, guanidine and the like.

Cultivation of *Streptomyces lydicus* ssp. *tanzanius* NRRL 18036 may be carried out in a wide variety of liquid culture media. Media which are useful for the production of LL-E19020 alpha and beta include an assimilable source of carbon, such as dextrin, sucrose, molasses, glycerol, etc.; an assimilable source of nitrogen such as protein, protein hydrolysate, polypeptides, amino acids, corn steep liquor, etc.; and inorganic anions and cations, such as potassium, sodium, ammonium, calcium, sulfate, carbonate, phosphate, chloride, etc. Trace elements such as boron, molybdenum, copper, etc., are supplied as impurities of other constituents of the media. Aeration in tanks and bottles is supplied by forcing sterile air through or onto the surface of the fermenting medium. Further agitation in tanks is provided by a mechanical impeller. An antifoam agent such as silicone oil may be added as needed.

Thus, in a preferred aspect of the invention we provide a process for separating LL-E19020 alpha and LL-E19020 beta from an aqueous solution thereof in admixture with impurities, which comprises the steps of recovering the antibiotics from the fermentation broth by adjustment of the pH with acid followed by dilution of the broth with a solvent such as methyl alcohol, filtering through diatomaceous earth followed by a water wash and filtering the combined filtrate and wash through a column of polystyrene divinylbenzene resin. The adsorption to the adsorbent can be accomplished either by a column method or by a batch method, the former is preferable. Preferred is a suitable nonionic adsorption resin(high porous copolymer) such as HP-20 resin produced by Mitsubishi Chemical, 277 Park Avenue, New York, N.Y. 10017. The HP-20 column is then washed with water and by aqueous solutions of 20, 40, 60, and 80% acetone followed by 100% acetone. Fractions are collected. The volatiles are evaporated from each fraction and the resulting concentrates are freeze-dried. This freeze-dried material is typically 50% pure LL-E19020 alpha or beta, and as such represents a higher quality intermediate to be used in the subsequent purification steps. Typically this results in a higher thoughput of material and a better overall yield of pure components.

Further purification of the material can be accomplished by high pressure liquid chromatography using a twelve to fifteen (12-15) liter reverse-phase column ($C_{18}$ bonded phase nominal 80 micron), eluting with (35 to 65%) 0.1M ammonium acetate pH 4.5/acetonitrile or 0.1% to 1% aqueous acetic acid (35 to 65%), or other suitable chromatographic methods. This chromatographic system produces 80-85% pure LL-E19020 alpha and pure LL-E19020 beta.

We have found the process according to the invention to be especially suitable for use with LL-E19020 alpha and beta.

In the present invention, a nonionic adsorption resin(high porous polymer) is used as the product adsorbent. Typical examples thereof include styrene-divinylbenzene type copolymers, substituted styrene-divinylbenzene type copolymers; methacrylic acid type polymers, styrene-allylacrylate type copolymers, other vinyl polymers or copolymers, and the like polymers which have been formed into granules. As an index to the porosity of a nonionic adsorption resin, there is used the specific surface area. A nonionic adsorption resin having a specific surface area of 30-2,000 $m^2/g$ are suitably used and those having the area of 100-1,000 $m^2/g$ are particularly preferable. The adsorption of LL-E19020 alpha and LL-E19020 beta to a nonionic adsorption resin is estimated to be caused mainly by van der Waals force. As specific examples of such adsorbents, there may be mentioned Diaion HP-10, HP-20, HP-21, HP-30, HP-40, HP-50, SP-206, SP-207, SP-800, SP-900, HP-MG1MG and HP-MG2MG (all mfd. by Mitsubishi Chemical Industries Ltd.) and Amberlite XAD-1, XAD-2, XAD-4, XAD-5 and XAD-7 (all mfd. by Rohm and Haas Co.) and Amberchrom CG161M (mfd. by Toso-Haas), but are not limited thereto. With regard to a nonionic adsorption resin used suitably in the process of the present invention, detail description are given, for example, in the following references:

I & EC Product Research and Development, 7, 107(1968);

"Amberlite XAD", published by Japan Organo Co., Ltd.;

U.S. Pat. No. 3,725,400.

Preferred is a styrene divinylbenzene highly porous copolymer resin such as HP-20 produced by Mitsubishi Chemical 277 Park Avenue, New York, N.Y. 10017.

We have used the method according to the invention to develop a process suitable for the purification of antibiotics LL-E19020 alpha and beta present in the fermentation broth obtained from strains of *Streptomyces lydicus* ssp. *tanzanius* NRRL 18036 producing LL-E19020 alpha and LL-E19020 beta. The new process involves an initial partial purification of the fermented antibiotic by pH adjustment, solvent dilution, filtration and adsorption chromatography on a styrene divinylbenzene resin followed by HPLC final purification.

The process is particularly suitable for LL-E19020 alpha and LL-E19020 beta which, because of experimental work is frequently produced on a very large scale.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

Inoculum Preparation

A typical medium used to grow the primary inoculum is prepared according to the following formula:

| | |
|---|---|
| Dextrose | 1.0% |
| Dextrin | 2.0% |
| Yeast extract | 0.5% |
| NZ Amine A | 0.5% |
| Calcium carbonate | 0.1% |
| Water qs | 100.0% |

NOTE: NZ Amine A is a pancreatic digest of casein, registered trademark of Scheffield Chemical, Norwich, N.Y.

This medium is sterilized and 100 ml, in a 500 ml flask, is inoculated with *Streptomyces lydicus* ssp. tanzanius NRRL 18036. The medium is then placed on a rotary shaker and incubated at 28° C. for 48 hours providing a primary inoculum. This primary inoculum is then used to inoculate 10 liters of the same sterile medium in an agitated and aerated bottle except that 0.3% v/v silicone antifoam is also added. This culture is grown for 24 hours providing secondary inoculum. This secondary inoculum is then used to inoculate 300 liters of the same sterile medium in a tank. This culture is grown at 32° C. for 44 hours with a sterile air flow of 200 liters per minute and agitation by an impeller driven at 200 rpm, providing a tertiary inoculum.

EXAMPLE 2

Fermentation

A fermentation medium of the following formulation is prepared:

| Dextrin | 7.0% |
|---|---|
| Dextrose | 0.5% |
| Soy flour | 1.5% |
| Corn Steep liquor | 0.5% |
| Calcium carbonate | 0.5% |
| Silicone antifoam | 0.3% |
| Water qs | 100.0% |

This medium is sterilized and is then inoculated with 150 liters of tertiary inoculum from Example 1 to a final volume of 1500 liters. The fermentation is conducted at 30° C. with a sterile air flow of 0.6 liters of air per liter of mash per minute and agitation by an impeller driven at 100-110 rpm for 123 hours, at which time the mash is harvested.

EXAMPLE 3

A fermentation medium of the following formulation is prepared:

| Dextrin | 7.0% |
|---|---|
| Dextrose | 0.5% |
| Soy flour | 1.5% |
| Corn steep liquor | 0.5% |
| Calcium carbonate | 0.5% |
| Silicone antifoam | 0.3% |
| Water qs | 100.0% |

This medium is sterilized and is then inoculated with 300 liters of tertiary inoculum similarly prepared as in Example 1 to a final volume of 3000 liters. The fermentation is conducted at 28° C. with a sterile air flow of 0.65 liters of air per liter of mash per minute and agitation by an impeller driven at 100-110 rpm for 89 hours, at which time the mash is harvested.

EXAMPLE 4

Isolation and Purification of LL-E19020 Alpha and Beta

The harvest mash from a fermentation conducted as described in Example 2 and Example 3, making a total volume of 2570 liters, is diluted with 28 liters of toluene. The pH is adjusted to 4.5 using 11 liters of concentrated hydrochloric acid. While stirring, 1950 liters of methyl alcohol is added. Stirring is continued over 6 hours and the pH is continuously monitored. To the mixture is added 250 pounds of diatomaceous earth followed by stirring for 15 minutes. The mixture is filtered through a filter press with the press washed with a volume of 15% of methyl alcohol based on original mash volume. The total volume collected is 4265 liters. To an 80 gallon HP-20 column previously prepared by washing the resin with 600 liters of acetone and 900 liters of deionized water and which is subsequently flushed with 300 liters of deionized water at a rate of 2 to 3 liters/minute immediately before use is added the above 4265 liters of eluate at a rate of 3 to 4 liters/minute. The total collected effluent is 4400 liters. The column is washed with 600 liters of deionized water at a rate of 4 to 5 liters/minute. The column is washed with a solution made from 480 liters of deionized water and 120 liters of acetone at a rate of 2 to 3 liters/minute to afford four 150 liter fractions which are collected and labeled F1–F4. The column is further washed with a solution made from 360 liters of deionized water and 240 liters of acetone at a rate of 2 to 3 liters/minute. The four 150 liter fractions collected are labeled F5–F8. Further washing of the column with a solution made from 240 liters of water and 360 liters of acetone affords four 150 liter collected fractions designated as F9–F12. The column is further washed with a solution made from 120 liters of deionized water and 480 liters of acetone to afford four 150 liters collected fractions designated as F13–F16. The column is finally washed with 600 liters of acetone and the four 150 liter fractions collected are designated as F17–F20. Each of the active 150 liter fractions is separated to 30 to 40 liters using a 50 gallon still and further evaporated in a rotary evaporator to 6 to 8 liters. Fractions F10 to F15 are freeze dried to give the following solids:

| F10 | 420.9 g |
|---|---|
| F11 | 142.5 g |
| F12 | 624.5 g |
| F13 | 38.9 g |
| F14 | 464.1 g |
| F15 | 111.3 g |

Fractions 11-15 are approximately 50% LL-E19020 alpha by weight, and thus represent at least a two-fold improvement in purity over the intermediate obtained in the original process.

Fractions F11, F13, F15 are combined and applied to a 12 liter reverse phase column ($C_{18}$ bonded phase 55 to 105 micron, 80 nominal particle size) and eluted with 41% acetonitrile in 1% aqueous acetic acid. Twenty five 20 liter fractions are collected (F1 to F25) followed by washing the column with three 20 liter methanol washes. The washes are evaporated to afford E19020 beta. Fractions F14 to F25 are combined and extracted with 120 liters of methylene chloride. The organic layer is separated, evaporated and combined with nine other runs of the same size. The concentrates are further concentrated to syrups and dissolved in t-butanol and freeze dried to afford 999.9 g of E19020 alpha of 85% purity as determined by HPLC.

We claim:

1. A process for producing antibiotics LL-E19020 alpha having the structure:

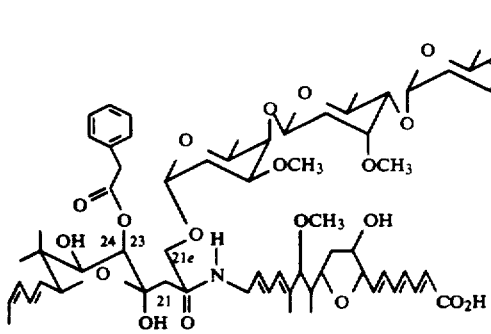

and LL-E19020 beta having the structure:

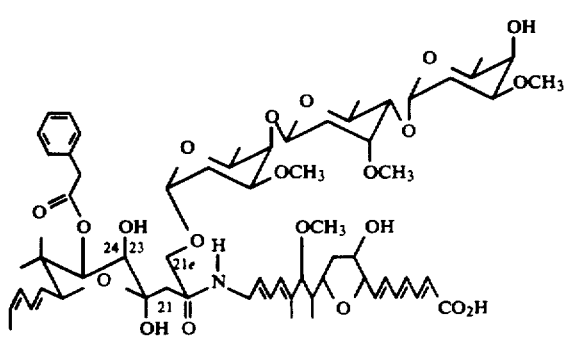

which comprises recovering the products produced by fermentation of a strain of *Streptomyces lydicus* ssp. *tanzanius* NRRL 18036 in an aqueous nutrient medium containing assimilable sources of carbon and nitrogen under submerged aerobic conditions by;
  (a) adsorbing the antibiotics on a nonionic adsorption resin;
  (b) separating the resin from the aqueous medium;
  (c) eluting the antibiotics from the resin with suitable solvent mixture;
  (d) purifying the fractions collected in step c by high pressure liquid chromatography on a suitable support with a suitable solvent mixture.

2. A process for producing antibiotics LL-E19020 alpha having the structure:

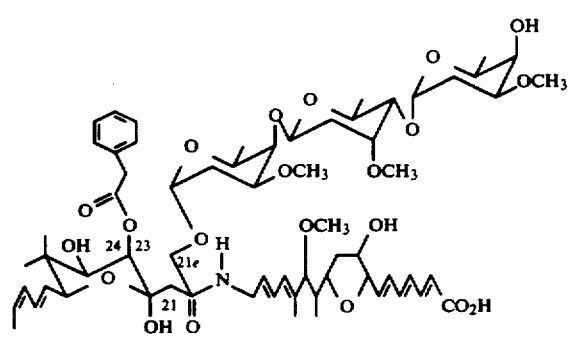

and LL-E19020 beta having the structure:

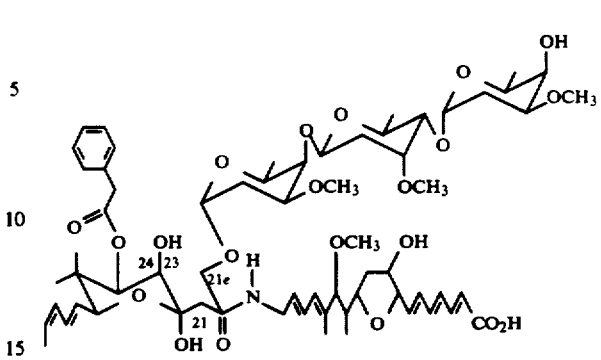

which comprises recovering the products produced by fermentation of a strain of *Streptomyces lydicus* ssp. *tanzanius* NRRL 18036 in an aqueous nutrient medium containing assimilable sources of carbon and nitrogen under submerged aerobic conditions by;
  (a) adsorbing the antibiotics on a nonionic adsorption resin column with a suitable solvent mixture;
  (b) eluting the resin column with a suitable solvent mixture and collecting fractions;
  (c) purifying the fractions collected in step b by high pressure liquid chromatography on a suitable support with a suitable solvent mixture.

3. A process according to claim 1 wherein the antibiotics adsorbed to the adsorbent are eluted with a water miscible organic solvent.

4. A process according to claim 1 wherein impurities and by-products other than the antibiotics are removed by elution with water prior to said elution of the antibiotics adsorbed to the adsorbent.

5. A process according to claim 1 wherein the suitable solvent mixture in step c is acetone-water.

6. A process according to claim 1 wherein the suitable support in step d is a reverse phase column ($C_{18}$ bonded phase 55 to 105 micron particle size).

7. A process according to claim 1 wherein the suitable solvent mixture in step d is aqueous ammonium acetate-acetonitrile at pH 4.5, or 0.1% or 1% aqueous acetic acid-acetonitrile.

8. A process according to claim 2 wherein the antibiotics adsorbed to the adsorbent are eluted with a water miscible organic solvent.

9. A process according to claim 2 wherein impurities and by-products other than the antibiotics are removed by elution with water prior to said elution of the antibiotics adsorbed to the adsorbent.

10. A process according to claim 2 wherein the suitable solvent mixture in step b is acetone-water.

11. A process according to claim 2 wherein the suitable support in step b is a reverse phase column ($C_{18}$ bonded phase 55 to 105 micron particle size).

12. A process according to claim 2 wherein the suitable solvent mixture in step c is aqueous ammonium acetate-acetonitrile at pH 4.5, or 0.1% or 1% aqueous acetic acid-acetonitrile.

* * * * *

UNITED STATES PATENT AND TRADEMARK OFFICE
CERTIFICATE OF CORRECTION

PATENT NO. : 5,188,945
DATED : February 23, 1993
INVENTOR(S) : Guy T. Carter, David R. Williams, Fernando Pinho It is certified that error appears in the above-indentified patent and that said Letters Patent is hereby corrected as shown below:

At column 1, lines 20-31; column 7, lines 1-15 and column 7, lines 47-60 delete the recited structure "
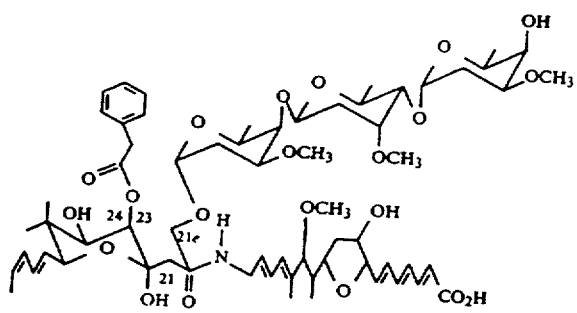
"

and insert the following structure therefor:

--
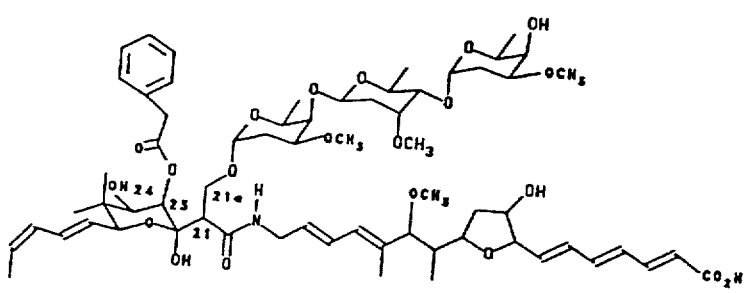
--

UNITED STATES PATENT AND TRADEMARK OFFICE
CERTIFICATE OF CORRECTION

PATENT NO. : 5,188,945
DATED : February 23, 1993
INVENTOR(S) : Guy T. Carter, David R. Williams, Fernando Pinho Page 2 of 3

It is certified that error appears in the above-indentified patent and that said Letters Patent is hereby corrected as shown below:

At column 1, lines 36-49; column 7, lines 17-30 and column 8 lines 4-15, delete the recited structure:

"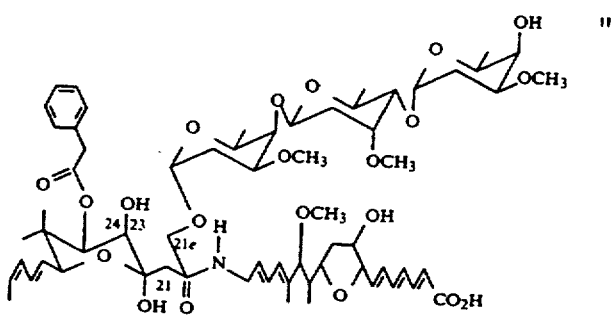"

UNITED STATES PATENT AND TRADEMARK OFFICE
CERTIFICATE OF CORRECTION

PATENT NO. : 5,188,945
DATED : February 23, 1993
INVENTOR(S) : Guy T. Carter, David R. Williams, Fernando Pinho It is certified that error appears in the above-indentified patent and that said Letters Patent is hereby corrected as shown below:

and insert the following structure:

--                                                                              --

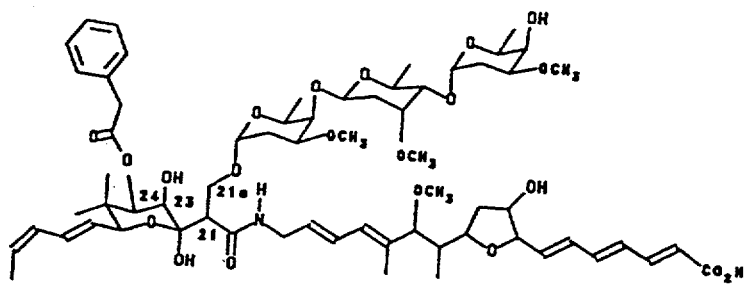

Signed and Sealed this

Sixteenth Day of May, 1995

*Attest:*

BRUCE LEHMAN

*Attesting Officer*     *Commissioner of Patents and Trademarks*